United States Patent [19]
Soloshonok et al.

[11] Patent Number: 5,939,588
[45] Date of Patent: Aug. 17, 1999

[54] ASYMMETRIC FLUORINE-CONTAINING PRIMARY AMINES AND THEIR PREPARATION

[75] Inventors: Vadim A. Soloshonok, Aichi; Taizo Ono, Gifu; Takashi Abe, Aichi, all of Japan

[73] Assignee: Agency of Industrial Science and Technology, Tokyo, Japan

[21] Appl. No.: 08/992,085

[22] Filed: Dec. 17, 1997

[30] Foreign Application Priority Data

Dec. 19, 1996 [JP] Japan .................................. 8-355198

[51] Int. Cl.[6] .................................................. C07C 211/00
[52] U.S. Cl. ........................... 564/366; 564/470; 564/471
[58] Field of Search .................................... 564/414, 415, 564/470, 471, 472, 366

[56] References Cited

PUBLICATIONS

W.R. Nes, et al., J. Am. Soc., vol. 72, pp. 5409–5413, Dec. 1950, "Amine and Enol Derivatives of 1,1,1–Trifluoropropane$^1$".

Vadim A. Soloshonok, et al., "A Practical Route to Fluoroalkyl–and Fluoroarylamines by Base–Catalyzed [1,3]–Proton Shift Reaction," Tetrahedron Letters, vol. 35, No. 19, (1994), pp. 3119–3122.

Vadim A. Soloshonok, et al., "Biomimetic Base–Catalyzed [1,3]–Proton Shift Reaction. A Practical Synthesis of β–Fluoroalkyl–β–Amino Acids," Tetrahedron, vol. 52, No. 20, (1996), pp. 6953–6964.

Vadim A. Soloshonok, et al., "The Effect of Substituents on the Feasibility of Azomethine–Azomethine Isomerization: New Synthetic Opportunities for Biomimetic Transamination," Tetrahedron, vol. 52, No. 47, (1996), pp. 14701–14712.

Vadim A. Soloshonok, et al., "The Effect of Substituents on the Feasibility of [1,3]–Proton Shift Reaction: New Synthetic Opportunities," Synlett, No. 9, (Sep., 1996), pp. 919–921.

Taizo Ono, et al., "Biomimetic Reductive Amination of Fluoro Aldehydes and Ketones via [1,3]–Proton Shift Reaction. Scope and Limitations," The Journal of Organic Chemistry, vol. 61, No. 19, (1996), pp. 6563–6569.

Vadim A. Soloshonok, et al., "Catalytic Asymmetric Synthesis of β–Fluoroalkyl–β–Amino Acids Via Biomimetic [1,3]–Proton Shift Reaction," Tetrahedron Letters, vol. 35, No. 28, (1994), pp. 5063–5064.

*Primary Examiner*—Samuel Barts
*Attorney, Agent, or Firm*—Oblon, Spivak, McClelland, Maier & Neustadt, P.C.

[57] ABSTRACT

The present invention, which is aimed at providing a novel reaction for converting a fluorine-containing carbonyl compound to an asymmetric fluorine-containing primary amine, relates to a method in which a Schiff base obtained by the condensation of a fluorine-containing carbonyl compound and an asymmetric amine ((S)- or (R)-1-phenylethylamine) is treated in the presence of an appropriate organic base to hydrolyze a tautomeric imine obtained by asymmetrically performing an enzyme-like transamination reaction, yielding an asymmetric fluorine-containing amine.

7 Claims, No Drawings

ASYMMETRIC FLUORINE-CONTAINING PRIMARY AMINES AND THEIR PREPARATION

FIELD OF THE INVENTION

The present invention provides a novel reaction for converting a fluorine-containing carbonyl compound to an asymmetric fluorine-containing amine. More particularly, the present invention provides a general method of synthesis in which a Schiff base obtained by the condensation of a fluorine-containing carbonyl compound and an asymmetric amine ((S)- or (R)-1-phenylethylamine) is treated in the presence of an appropriate organic base to hydrolyze a tautomerized imine obtained by asymmetrically performing an enzyme-like transamination reaction, yielding an asymmetric fluorine-containing amine. The resulting asymmetric fluorine-containing amine is known to possess physiological activity by itself, and is also important as a key intermediate of drugs, agricultural chemicals, liquid crystals, and the like. In addition, it is already known to be used as a reagent for determining optical purity.

BACKGROUND OF THE INVENTION

It is known that transamination reactions are performed by transaminases occurring widely in the biosphere. In practical terms, they play an important role in the biosynthesis of amino acids and intravital amines and are useful as synthetic means, but since these are enzyme reactions, there are significant limitations as regards the substrate, making it impossible to devise general reactions. However, in an article related to the fluorine-containing carbonyl compounds expressed by General Formula 1 below, Soloshonok at al. have recently reported that the corresponding aldimine can be obtained by subjecting an enamine obtained by reaction with benzylamine to a [1,3] proton shift reaction in the presence of an organic chlorine such as triethylamine. Following the publication of this article, it has been acknowledged that transamination reactions performed using the above reaction can be useful as a general method for synthesizing fluorine-containing amine compounds (Tetrahedron Lett., Vol. 35, No. 19, pp. 3119–3122, 1994; Tetrahedron, Vol. 52, No. 20, pp. 6953–6964, 1996; ibid., Vol. 52, No. 47, 14701–14712, 1996; Synlett., No. 9, pp. 919–921, 1996; J. Org. Chem., Vol. 61, No. 19, 6563–6569, 1996).

Transamination reactions performed using aminomethylpyridine are also reported at length in recently published patent literature. It has been accepted that such enzyme-like transamination reactions performed using [1,3] proton shift reactions can be widely used as general methods for synthesizing fluorine-containing amines. However, there is only one report concerning the use of (−)-cinchonidine in a method for performing such a [1,3] proton shift reaction by making use of asymmetric amines (Tetrahedron Lett., Vol. 35, No. 28, pp. 5063–5064, 1994), and no other information on the subject is known to exist. Demand for asymmetric fluorine-containing amines is strong because fluorine-containing amines are used as intermediates of drugs, agricultural chemicals, and reagents for determining optical purity. In the past, however, such amines were extremely expensive because they were obtained by optical resolution from racemic modifications. A need therefore existed for the development of a simple method for synthesizing fluorine-containing amines.

As a result of a painstaking effort involved in extensive research conducted under the conditions described above, aimed at developing an asymmetric transamination reaction in view of the aforementioned prior art, and centered on asymmetric (R)- or (S)-phenylethylamines, the inventors discovered that the target asymmetric transamination reactions can be conducted without initiating racemization by performing these reactions using an appropriate organic base as a solvent. The inventors devised the present invention on the basis of this discovery.

SUMMARY OF THE INVENTION

An object of the present invention is to provide a novel reaction for converting a fluorine-containing carbonyl compound to an asymmetric fluorine-containing primary amine.

The present invention relates to a manufacturing method in which a Schiff base obtained by the condensation of a fluorine-containing carbonyl compound and an asymmetric primary amine ((S)- or (R)-1-phenylethylamine) is treated in the presence of an appropriate organic base to hydrolyze a tautomerized imine obtained by asymmetrically performing an enzyme-like transamination reaction, yielding an asymmetric fluorine-containing primary amine.

The use of an asymmetric transamination reaction in the present invention allows an asymmetric fluorine-containing primary amine to be easily synthesized using a fluorine-containing carbonyl compound as a starting material with high optical and chemical yields and under moderate conditions. The resulting asymmetric fluorine-containing primary amine is an important synthesis intermediate of drugs, agricultural chemicals, and the like.

DETAILED DESCRIPTION OF THE INVENTION

An object of the present invention is to develop an asymmetric transamination reaction and to provide a general method for synthesizing asymmetric fluorine-containing amines.

Aimed at attaining the stated object, the present invention is a method for manufacturing an asymmetric fluorine-containing amine from a fluorine-containing carbonyl compound characterized in that a Schiff base of a fluorine-containing carbonyl compound with an (R)- or (S)-1-phenylethylamine is treated with an appropriate organic base to perform an [1,3] proton shift reaction without initiating racemization, and the resulting tautomeric imine is hydrolyzed without being racemized.

Preferred embodiments of the present invention are a method for manufacturing an asymmetric fluorine-containing amine compound from a fluorine-containing carbonyl compound by an asymmetric transamination reaction wherein the fluorine-containing carbonyl compound is a linear or branched fluoroalkyl compound containing fluoroalkyl groups and having a carbon number of 1 to 16, and a method for manufacturing an asymmetric fluorine-containing amine compound from a fluorine-containing carbonyl compound by making use of an (R)- or (S)-1-phenylethylamine.

The present invention will now be described in further detail.

As described above, the present invention relates to a method of general synthesis in which a Schiff base of a fluorine-containing carbonyl compound with an (R)- or (S)-1-phenylethylamine is treated with an appropriate organic base to perform a [1,3] proton shift reaction without initiating racemization, and an asymmetric transamination reaction resembling an enzyme reaction is then performed by hydrolysis, yielding an asymmetric fluorine-containing amine compound from a fluorine-containing carbonyl compound under moderate conditions and without the use of a reductant.

No particular restrictions are imposed on the fluorine-containing carbonyl compounds referred to herein, and any appropriate compound may be used. However, the compounds expressed by General Formula 1 below are preferred. In addition, such fluorine-containing amine compounds are typified by the primary amine compounds expressed by General Formula 2 below, but the method of the present invention is not limited to these compounds and can be used with other compounds in the same manner.

The method of the present invention will now be described with reference to typical compounds.

Specifically, as a preferred example, the present invention provides a method of general synthesis in which a compound expressed by General Formula 1 below
Chemical Formula (1)

(where Rf is a linear or branched perfluoroalkyl group with a carbon number of 1 to 16, R is a linear or branched alkyl group or aralkyl group with a carbon number of 1 to 16, and the perfluoroalkyl group is a group in which all the hydrogens of the hydrocarbon groups are substituted by fluorine atoms) is condensed with an (R)- or (S)-1-phenylethylamine in the presence of an appropriate solvent to produce a Schiff base, then treated with an appropriate organic base, and subjected to a [1,3] proton shift reaction without initiating racemization; and an enzyme-like asymmetric transamination reaction is performed by hydrolyzing the resulting tautomeric imine under racemization-free conditions, yielding an asymmetric fluorine-containing amine compound expressed by General Formula 2 below
Chemical Formula (2)

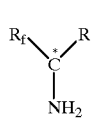

(where Rf is a linear or branched perfluoroalkyl group with a carbon number of 1 to 16, R is a linear or branched alkyl group or aralkyl group with a carbon number of 1 to 16, and the perfluoroalkyl group is a group in which all the hydrogens of the hydrocarbon groups are substituted by fluorine atoms).

Many of the fluorine-containing carbonyl compounds used as the starting materials in the present invention are commercially available. Those that are not available on the market can easily be synthesized by methods known from the literature (J. Am. Chem. Soc., Vol. 72, 5409, 1950). The fluorine-containing carbonyl compound thus obtained is dissolved, for example, in a halogenated hydrocarbon (such as chloroform, dichloromethane, or 1,2-dichloroethane), an ether-based solvent (such as ether, tetrahydrofuran, 1,2-dimethoxyethane, or diglyme), or, preferably, an aromatic hydrocarbon-based solvent (such as benzene, toluene, or xylene); an equal amount or an excess of (R)- or (S)-1-phenylethylamine is added thereto; and a reaction is conducted at room temperature or reflux temperature, whereby dehydrocondensation is performed and the corresponding Schiff base is obtained.

Dabco (1,4-Diazabicyclo [2,2,2] octane), DBU (1,8-Diazabicyclo [5,4,0] undec-7-ene), DBN (1,5-diazabicyclo [4,3,0] non-5-ene), triethylamine, or another organic base is added to the residue obtained by distilling off the solvent; and a [1,3] proton shift reaction is conducted at a temperature that does not initiate racemization. The appropriate temperature and time vary with the Schiff base of the substrate, but a temperature ranging from room temperature to about 60 degrees is preferred. Any base can probably be used as long as it is an organic base having approximately the same basicity as the bases described above; DBU affords good results in the examples described below. A person with ordinary skills in chemistry can easily find the appropriate conditions for any substrate not covered in the examples. The amount in which the organic base is added is about 0.1 to 10 equivalents, and preferably about 1 to 2 equivalents, with respect to the substrate.

After it has been confirmed by thin-layer chromatography or NMR that the reaction has been completed, an asymmetric tautomeric imine can be obtained by distilling off the material at a reduced pressure when triethylamine is used as an organic base, or by passing the material through a silica gel column to achieve removal when DBU is used. An asymmetric fluorine-containing amine is obtained by the hydrolysis of the resulting asymmetric imine. Hydrochloric acid, sulfuric acid, nitric acid, or another acid can be used to perform hydrolysis. The concentration of the acid may range from 1N to 6N, and 2 to 4N hydrochloric is preferred for use. The final product can be easily isolated by extraction, recrystallization, column chromatography with a silica gel, or another common chemical means used in organic synthesis.

The compounds expressed by the general formulas described above are merely preferred examples. The method of the present invention is not limited to these compounds alone and allows asymmetric fluorine-containing amine compounds to be obtained from other fluorine-containing carbonyl compounds. The present invention can be used as a general synthesis reaction for manufacturing asymmetric fluorine-containing amines from fluorine-containing carbonyl compounds.

EXAMPLES

The present invention will now be described in further detail through examples, but the present invention is not limited in any way by these examples.

In the examples that follow, the formation of asymmetrically transaminated compounds has been confirmed by NMR and MS. The enantiomer excess (ee) of the product was determined by HPLC using a chiral column (SUMICHIRAL OA-4500). The absolute configuration of the resulting asymmetric fluorine-containing amine was compared with the reported values by measuring optical rotation. All these types of data are shown here. The yield is isolation yield is all cases. $^1$H, $^{19}$F, and $^{13}$C-NMR was performed by conducting measurements at magnetic field strengths obtained at 299.95, 282.24, and 75.42 MHz, respectively.

Synthesis of the starting material Schiff base is expressed by General Formula 3 below Chemical Formula (3)

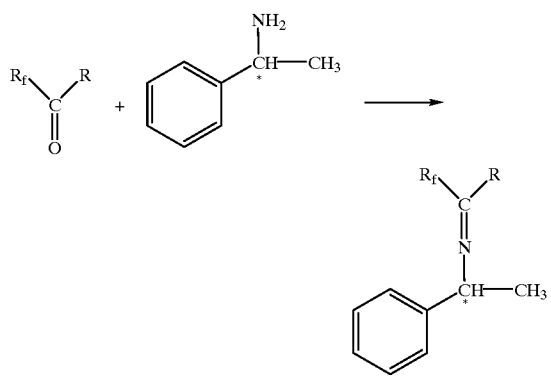

Reference Example 1
Schiff Base: (S)-N-1-Phenyl-2,2,2-T rifluoroethylidene)-1-Phenylethylamine (1a)

Trifluoromethylphenyl ketone (348 mq, 2 mmol) and (S)-1-phenylethylamine (242 mg, 2 mmol) were metered out into a 50-mL round-bottom flask, 20 mL benzene was added, a Dean-Stark trap was mounted, and the system was refluxed. The solvent was removed with the aid of an evaporator, and 1a was produced at a yield of 82%. Rf 0.45 (hex/AcOEt=4:1) $^1$H NMR d 1.44 (d, 3H, J=6.6 Hz), 4.54 (q,1H, J=6.6 Hz), 7.17–7.35 (m, 8H), 7.47–7.50 (m, 2H); $^{19}$F NMR d −71.63(s). $^{13}$C NMR d 24.53(s), 61.38(s), 119.77(q, $J_{CF}$=278.8 Hz), 126.45(s), 127.24(s), 127.60(s), 128.61(s). 128.77(s), 130.02(s), 130.56(s), 143.76(s), 156.58(q, $J_{CF}$=33.2 Hz). MS 277 (M, 7.6), 262 (M-Me, 2.1), 105(100). Anal. Calcd for $C_{16}H_{14}F_3N$: C, 69.31; H, 5.09; N, 5.05; F, 20.55. Found: C, 69.43; H, 5.19; N, 5.05; F, 20.33.

Reference Example 2
Schiff Base: (S)-N-(1,1,1-Trifluoro-3-Phenyl-Isopropylidene)-1-Phenylethylamine (1b)

1b was obtained with a yield of 98% in the same manner as 1a. Rf 0.45 (hex/AcOEt=4:1) $^1$H-NMR (CDCl$_3$) d 1.43 (d, 3H, J=6.6 Hz), 3.83 (AB, 2H, J=15.6 Hz), 4.83 (q, 1H, J=6.6 Hz), 7.09–7.12 (m, 2H), 7.25–7.32 (m, 8H); $^{19}$F NMR d −72.70(s); $^{13}$C NMR d 24.42(s), 33.19(s), 60.29(s), 119.95 (q, $J_{CF}$=279.4 Hz), 126.49(s), 127.08(s), 127.26(s), 128.24 (s), 128.58(s), 128.95(s), 134.22(s), 143.53(s), 155.49 (q, $J_{CF}$=32.5 Hz). MS 291 (M, 0.8), 276 (M-Me, 0.8), 105 (100). Anal. Calcd for $C_{17}H_{16}F_3N$: C, 70.09; H, 5.54; N, 4.81; F, 19.56. Found: C, 69.98; H, 5.55; N, 4.78; F, 19.61.

Reference Example 3
Schiff Base: (S)-N-(1,1,1-Trifluoroisopropylidene)-1-Phenylethylamine (1c)

1c was obtained with a yield of 74% in the same manner as 1a. Rf 0.46 (hex/AcOEt=4:1) $^1$H-NMR (CDCl$_3$) d 1.49 (d, 3H, J=6.6 Hz), 2.03(s, 3H), 4.71 (q, 1H, J=6.6 Hz), 7.25–7.38 (m, 5H); $^{19}$F NMR d −75.23(s); $^{13}$C NMR d 12.65(s), 24.31(s), 59.93(s), 119.87 (q, $J_{CF}$=278.5 Hz), 126.46(s), 127.20(s), 128.62(s), 143.75(s). 154.60 (q, $J_{CF}$=33.4 Hz). MS 215 (M, 1.8), 200 (M-Me, 2.1), 105(100).

Reference Example 4
Schiff Base: (S)-N-(1,1,1-Trifluoroisobutylidene)-1-Phenylethylamine (1d)

1d was obtained with a yield of 69% in the same manner as 1a. Rf 0.49 (hex/AcOEt=4:1) $^1$H-NMR (CDCl$_3$) d 1.14 (tq, 3H, J=7.8 Hz, J=0.6 Hz), 1.52 (d, 3H, J=6.6 Hz), 2.58 (q, 2H, J=7.8 Hz), 4.82 (q, 1H, J=6.6 Hz), 7.24–7.41 (m, 5H); $^{19}$F NMR d −73.20(s); $^{13}$C NMR d 11.28(s), 20.45(s), 24.87(s), 59.35(s), 120.18 (q, $J_{CF}$ =279.4 Hz), 126.37(s), 127.20(s), 128.60(s), 144.01(s). 158.79 (q, $J_{CF}$=33.8 Hz). MS 229 (M, 1.2), 214 (M-Me, 1.8), 105(100).

Reference Example 5
Schiff Base: (S)-N-(5,5,5,4,4,3,3-Heptafluoro-2-Pentylidene)-1-Phenylethylamine (1e)

1e was obtained with a yield of 57% in the same manner as 1a. Rf 0.46. $^1$H-NMR (CDCl$_3$) d 1.48 (q, 3H, J=6.6 Hz), 2.05 (t, 3H, J=0.9 Hz), 4.76 (q, 1H, J=6.6 Hz) 7.25–7.35 (m, 5H); $^{19}$F NMR d −80.63 (t, 3F, J=10.5 Hz), 116.76 (q, 2F, J=10.5 Hz), 126.22 (s, 2F); $^{13}$C NMR d 13.41(s), 24 .39(s), 60.45(s), 126.41(s), 127.17(s), 128.59(s), 143.78(s) ; Four types of carbons bonded to fluorines and carbons adjacent to these could not be identified due to coupling with fluorine atom nuclei. MS 315 (M, 0.6), 300 (M-CH3, 2.3), 105(100).

Example 1
(R)-2,2,2-Trifluoro-1-Phenylethylamine Hydrochloride

Schiff base 1a was dissolved in two equivalents of DBU, a reaction was allowed to occur for 4 hours at 19° C., and the DBU was then removed using a silica gel column. After being eluted from the silica gel column with the aid of a mixed solvent comprising hexane and ethyl acetate, the solvent was distilled off, yielding (R)-N-(1-phenylethylidene)-1-phenyl-2,2,2-trifluoroethylamine in the form of a 12:1 mixture of geometrical isomers. Rf 0.34 $^1$H-NMR (CDCl$_3$) d, Principal products: 2.18 (s, 3H), 5.08 (q, 1H, J=7.5 Hz), 7.27–7.53 (m, 8H), 7.92–7.95 (m, 2H); $^{19}$F-NMR (CDCl$_3$) d −74.90 (d, J=7.5 Hz); By-products: 2.44 (s, 3H), 4.68 (q, 1H, J=7.7 Hz); The effect of the principal products on the absorption of portions of aromatic nuclei was unclear.

$^{19}$F-NMR (CDCl$_3$) d −74.34 (d, $J_{HF}$=7.7 Hz). MS 277 (M, 53.2), 109(100). Anal. Calcd for $C_{16}H_{14}F_3N$:C, 69.31; H, 5.09; N, 5.05; F, 20.55. Found: C, 69.52; H, 5.12; N, 4.93; F, 20.39.

2 mL of 4NHCL was added to a solution obtained by dissolving the resulting mixture of geometrical isomers (262 mg, 0.95 mmol) in 3 mL of ether, and the system was agitated at room temperature. The fact that the reaction had been completed was confirmed by TLC, and the aqueous layer was separated out and washed with ether. The aqueous layer was evaporated to dryness at a reduced pressure, yielding a crystalline hydrochloride at a yield of 95%. $[\alpha]D^{25}$ −16.45 (c0.75, EtOH) $^1$H-NMR (CD$_3$CN/CD$_3$OD, 3/1) d 5.17 (d, 1H, $J_{H-F}$=7.5 Hz), 7.56 (s, 5H ); $^{19}$F NMR (CD$_3$CN/CD$_3$OD, 3/1) d −72.69 (d, $J_{H-F}$=7.5 Hz).

The enantiomer excess was determined by HPLC in terms of 3,5-dinitrobenzoylamide. Specifically, the hydrochloride obtained as described above was dissolved in 3 mL of dichloromethane, triethylamine (288 mg, 2.84 mmol) was then added, and the system was thoroughly agitated. A dichloromethane solution (1 mL) of 3,5-dinitrobenzoyl chloride (240 mg, 1.04 mmol) was added to the resulting solution, and the system was agitated for 20 minutes at room temperature, then concentrated with the aid of an evaporator, and dried in a vacuum, yielding a crystalline product (yield: 97%).

Rf 0.68 (n-hexane/AcOEt 3/1); $^1$H-NMR (acetone-d6) d 6.03 (quin, 1H, $J_{HH}$=8.7 Hz), 7.45–7.50 (m, 3H), 7.61–7.64 (m, 2H), 8.38 (d, 1H, $J_{HH}$=8.7 Hz), 8.99 (d, 2H, $J_{HH}$=2.4 Hz), 9.06 (t, 1H, $J_{HH}$=2.4 Hz). $^{19}$F-NMR (acetone-d6) d −72.30 (d, $J_{HF}$=8.7 Hz). MS 369 (M, 2.6), 349 (M-HF, 100).

The enantiomer excess was 87% ee, at determined by HPLC using SUMICHIRAL OA-4500 (hexane/di chloroethane/ethanol: 60/30/10, 1=254:18.47 parts (S)-enantiomer, 20.84 parts (R)-enantiomer (principal component)).

The absolute configuration of the product was determined based on the optical rotation of the free (R)-2,2,2-trifluoro-1-phenylethylamine. Specifically, 10 mL of dry ether and 4.3 g of triethylamine (21.3 mmol) were added to (R)-2,2,2-trifluoro- 1-phenylethylamine hydrochloride (4.8 g, 21.3 mmol), and the system was thoroughly agitated. The triethylamine hydrochloride that formed 10 hours later was removed by filtration. The filtrate was concentrated to dryness at a reduced pressure, yielding a free amine (3.85 g, 95.7%). bp 66 to 68° C. (2 mm Hg): $[\alpha]D^{25}$–17.72 (c 3.44, EtOH) (81% ee by HPLC); reported (S)-enantiomer values: $[\alpha]D^{25}$+24.11 (c 12.0 EtOH) (ref. 10a), reported (R)-2,2,2-trifluoro-1-phenylethylamine values: $[\alpha]D^{20}$–21.6 (c 3.1, EtOH) (ref. 10b); $^1$H NMR d 1.76 (br. s, 2H), 4.39 (q, 1H, J=7.2 Hz), 7.26–7.45 (m, 5H); $^{19}$F NMR d –77.22 (d, $J_{HF}$=7.2 Hz); $^{13}$C NMR d 57.91 (q, $J_{CF}$=29.9 Hz), 125.68 (q, $J_{CF}$=281.4 Hz), 127.81(s), 128.68(s), 128.96(s), 135.45 (q, $J_{CF}$=1.2 Hz).

Example 2

(R)-1,1,1-Trifluoro-3-Phenylisopropylamine Hydrochloride

Schiff base 1b was isomerized using two equivalents of DBU in the same manner as in Example 1, yielding (R)-N-(1- phenylethylidene)-1,1,1-trifluoro-3-phenyisopropylamine in the form of a 10:1 mixture of geometrical isomers. (4b): Rf 0.36; as a 10:1 mixture of geometric isomers. $^1$H-NMR (CDCl$_3$) d, Principal products: 1.55 (s, 3H), 3.03, 3.28 (ABX, 2H, $J_{AB}$=13.2 Hz, $J_{AX}$=2.4 Hz, $J_{BX}$=10.5 Hz), (4.25 (dqd, 1H, $J_{HH}$=10.5 Hz, $J_{HF}$=6.8 Hz, $J_{HH}$=2.4 Hz), 7.11–7.41 (m, 8H), 7.69– 7.73 (m, 2H). $^{19}$F-NMR d –75.30 (d, $J_{HF}$=6.8 Hz); By-products: 2.24 (s, 3H), 3.01 (m, 2H), 3.81 (m, 1H); The effect of the principal products on the absorption of portions of aromatic nuclei was unclear. $^{19}$F NMR d –74.89 (d, $J_{HF}$=7.1 Hz). MS 291 (M, 3.4), 276 (M-Me, 26.5), 159(100). Anal. Calcd for $C_{17}H_{16}F_3N$: C, 70.09; H, 5.54; N, 4.81; F, 19.56. Found: C, 70.21; H, 5.59; N, 4.75; F, 19.39.

The resulting mixture of geometrical isomers was hydrolyzed in the same manner as in Example 1, yielding a crystalline hydrochloride at a yield of 93%. $[\alpha]D^{25}$+22.19 (c 1, EtOH) $^1$H-NMR (CD$_3$CN) d 3.25, 3.43 (ABX, 2H, $J_{AB}$=14.7 Hz, $J_{AX}$=6.6 Hz, $J_{BX}$=7.6 Hz), 4.31 (dqd, 1H, $J_{H-H}$=7.6, $J_{H-F}$=7.1, $J_{H-H}$=6.6 Hz), 7.30–7.43 (m, 5H), 9.05 (br. s, 3H); $^{19}$F-NMR(CD$_3$CN)d –71.39 (d, $J_{H-F}$=7.1 Hz).

The resulting hydrochloride was converted in the same manner as in Example 1 to a 3,5-dinitrobenzoylamido derivative, N-(3,5-dinitrobenzoyl)-1,1,1-trifluoro-3-phenylisopropylamine (yield: 94%). Rf 0.69 (n-hexane/AcOEt 3/1); $^1$H-NMR (acetone-d6) d 3.03, 3.32 (ABX, 2H, $J_{AB}$=14.4 Hz, $J_{AX}$=3.6 Hz, $J_{BX}$=11.7 Hz), 5.12 (ddqd, 1H, $J_{HH}$=11.7 Hz, $J_{AX}$=9.9 Hz, $J_{HF}$=6.8 Hz, $J_{HH}$=3.6 Hz), 7.21–7.37 (m, 5H), 7.83 (d, 1H, $J_{HH}$=9.9 Hz), 8.80 (d, 2H, $J_{HH}$=2.1 Hz), 9.01 (t, 1H, $J_{HH}$=2.1 Hz). 19-NMR (acetone-d6) d –74.66 (d, $J_{HF}$=6.8 Hz). MS 383 (M, 2.6), 172(100).

The enantiomer excess was 87% ee, as determined by HPLC using SUMICHIRAL OA-4500 (hexane/di chloroethane/ethanol: 60/30/10, 1=254:17.25 parts (S)-enantiomer, 21.68 parts (R)-enantiomer (principal component)).

Example 3

(R)-1,1,1-Trifluoroisopropylamine Hydrochloride

Schiff base 1c was isomerized using 1.5 equivalents of DBU in the same manner as in Example 1, yielding (R)-N-(1- phenylethylidene)-1,1,1-trifluoroisopropylamine in the form of a 12:1 mixture of geometrical isomers. Rf 0.26 $^1$H-NMR (CDCl$_3$) d, Principal products: 1.35 (d, 3H, J=6.9 Hz), 2.28 (s, 3H), 4.17 (sep, 1H, $J_{HH}$=$J_{HF}$=6.9 Hz), 7.38–7.40 (m, 3H), 7.82–7.85 (m, 2H). $^{19}$F-NMR (CDCl$_3$) d –77.66 (d, $J_{HF}$=6.8 Hz); By-products: 1.20 (d, 3H, J=6.6 Hz), 2.35 (s, 3H), 3.79 (sep, 1H, $J_{HH}$=$J_{HF}$=6.6 Hz); The effect of the principal products on the absorption of portions of aromatic nuclei was unclear. $^{19}$F-NMR (CDCl$_3$) d –76.65 (d, $J_{HF}$=6.6 Hz). MS 215 (M, 24.8), 200 (M-Me, 43.1), 104(100)

The resulting mixture of geometrical isomers was hydrolyzed in the same manner as in Example 1, yielding a crystalline hydrochloride at a yield of 94%. $[\alpha]D^{25}$ –2.94 (c 1, MeOH); $[\alpha]D^{25}$–4.24 (c 1, EtOH), $^1$H NMR (CD$_3$CN/CD$_3$OD, 3/1) d 1.49, (dq, 3H, $J_{H-H}$=6.9, $J_{H-F}$=0.6 Hz), 4.08 (dd, 1H, $J_{H-H}$=6.9, $J_{H-F}$=6.7 Hz); $^{19}$F NMR (CD$_3$CN/CD$_3$OD, 3/1) d –75.67 (d, $J_{H-F}$=6.7 Hz).

The resulting hydrochloride was converted in the same manner as in Example 1 to a 3,5-dinitrobenzoylamido derivative, N-(3,5-dinitrobenzoyl)-1,1,1-trifluoroisopropylamine (yield: 91%). Rf 0.55 (n-hexane/AcOEt 3/1); $^1$H-NMR (MeCN-d3) d 1.48 (d, 3H, $J_{HH}$=7.2 Hz), 4.95 (ddq, 1H, $J_{HH}$=7.2 Hz, $J_{HH}$=9.8 Hz, $J_{HF}$=7.1 Hz), 7.80 (d, 1H, $J_{HH}$=9.8 Hz), 9.01 (d, 2H, $J_{HH}$=2.1 Hz), 9.05 (t, 1H, $J_{HH}$=2.1 Hz). $^{19}$F-NMR (MeCN-d3) d –78.08 (d, $J_{HF}$=7.1 Hz). $^{13}$C NMR (MeCN-d3) d 12.98 (q, $J_{CF}$=2.0 Hz), 47.45 (q, $J_{CF}$=31.4 Hz), 121.50(s), 125.85 (q, $J_{CF}$=280.8 Hz), 127.97(s), 127.20(s), 136.73(s), 148.81(s), 163.10(s). MS 307 (M, 3.2), 86 (M-HF, 100).

The enantiomer excess was 98% ee, as determined by HPLC using SUMICHIRAL OA-4500 (hexane/di chloroethane/ethanol: 60/30/10, 1=254:9.997 parts (S)-enantiomer, 15.142 parts (R)-enantiomer (principal component)).

Example 4

Schiff base 1d was isomerized using 1.5 equivalents of DBU in the same manner as in Example 1, yielding (R)-N-(1- phenylethylidene)-1,1,1-trifluoroisobutylamine in the form of a 16:1 mixture of geometrical isomers. Rf 0.27 $^1$H-NMR d, Principal products: 1.91 (tq, 3H, J=7.5 Hz, J=0.6 Hz), 1.86, 1.97 (ABXY, 2H, $J_{AB}$=13.5 Hz, $J_{AX}$=3.9 Hz, $J_{BX}$=8.9 Hz, $J_{AY}$=$J_{BY}$=7.5 Hz), 2.29 (s, 3H), 4.02 (dqd, 1H, $J_{HH}$=8.9 Hz, $J_{HF}$=7.0 Hz, $J_{HH}$=3.9 Hz), 7.39–7.42 (m, 3H), 7.82–7.85 (m, 2H). $^{19}$F-NMR d –74.84 (d, $J_{HF}$=7.0 By-products: 0.76 (td, 3H, J=7.5 Hz, J=0.6 Hz), 2.38 (s, 3H), 3.63 (m, 1H); The effect of the principal products on the absorption of aromatic nuclei and methylene (ABXY) portions was unclear. er. $^{19}$F-NMR d –74.60 (d, $J_{HF}$=7.1 Hz). MS 229 (M, 6.8), 214 (M-Me, 58.9), 104(100).

The resulting mixture of geometrical isomers was hydrolyzed in the same manner as in Example 1, and the hydrochloride was then converted to a 3,5-dinitrobenzoylamido derivative, N-(3,5-dinitrobenzoyl)-1,1,1-trifluoroisobutylamine (yield: 98%) without being isolated. Rf 0.63 (n-hexane/AcOEt 3/1); $^1$H-NMR (MeCN-d3) d 1.02 (td, 3H, $J_{HH}$=7.2 Hz, $J_{HH}$=0.6 Hz), 1.79 (m, 1H), 1.94 (m, 1H), 4.75 (m, 1H), 7.71 (d, 1H, $J_{HH}$=9.2 Hz), 8.99 (d, 2H, $J_{HH}$=2.1 Hz), 9.07 (t, 1H, $J_{HH}$=2.1 Hz). $^{19}$F-NMR (MeCN-d3) d –74.73 (d, $J_{HF}$=7.1 Hz). $^{13}$C NMR (MeCN-d3) d 10.18(s), 21.54 (q, $J_{CF}$=1.96 Hz), 53.80 (q, $J_{CF}$=30.1 Hz), 122.49(s), 126.58 (q, $J_{CF}$=280.4 Hz), 128.94(s), 127.20(s), 137.54(s), 149.76(s), 164.69(s). MS 321 (M, 9.7), 306(M-CH3, 3.1), 75(100).

The enantiomer excess was 87% ee, as determined by HPLC using SUMICHIRAL OA-4500 (hexane/di chloroethane/ethanol: 60/30/10, 1=254:8.617 parts (S)-enantiomer, 14.800 parts (R)-enantiomer (principal component)).

Example 5

Schiff base 1e was isomerized using 1.5 equivalents of DBU in the same manner as in Example 1, yielding (R)-N-(1- phenylethylidene)-(5,5,5,4,4,3,3-heptafluoro-2-pentyl) amine. Rf 0.31; $^1$H-NMR d: 1.36 (dd, 3H, J=6.6 Hz, J=0.6 Hz), 2.28 (s, 3H), 4.35 (m, 1H), 7.38–7.42 (m, 3H), 7.81–7.84 (m, 2H). $^{19}$F-NMR d −81.44 (dd, J=11.9 Hz, J=8.5 Hz), 118.74, 125.62 (ABm, 2F, $J_{AB}$=275.5 Hz), 125.03, 126.79 (ABXY, 2F, $J_{AB}$=291.0 Hz, $J_{AX}$=$J_{BX}$=12.2 Hz, $J_{AY}$=7.1 Hz); $^{13}$C-NMR d 13.39(m), 15.03(s), 57.13 (dd, $J_{CF}$=20.1 Hz, $J_{CF}$=26.8 Hz), 125.3 1(m), 126.95(s), 126.32 (s), 128.90(m), 130.25(s), 140.17(s), 167.01(s). MS 315 (M, 12.6), 300 (M-CH3, 12.6), 146(M-C3F7, 100).

The resulting compound was hydrolyzed in the same manner as in Example 1, and the hydrochloride was then converted to a 3,5-dinitrobenzoylamido derivative, N-(3,5-dinitrobenzoyl)-5,5,5,4,4,3,3-heptafluoro-2-pentylamine (yield: 91%), without being isolated. Rf 0.26; $^1$H-NMR (MeCN-d3) d 1.02 (dm, 3H, $J_{HH}$=7.2 Hz), 5.15 (m, 1H), 7.78 (d, 1H, $J_{HH}$=8.7 Hz), 8.96 (d, 2H, $J_{HH}$=2.1 Hz), 9.06 (t, 1H, $J_{HH}$=2.1 Hz). $^{19}$F-NMR d −80.34 (t, J=10.5 Hz), 118.73, 120.97 (ABm, 2F, $J_{AB}$=278.9 Hz), 125.06 (dd, 2F, J=15.5 Hz, J=7.1 Hz); $^{13}$C-NMR d 13.92(m), 46.88 (dd, $J_{CF}$=21.9 Hz, $J_{CF}$=27.0 Hz), 110.23(m), 116.30 (m), 122.49(s), 128.90 (m), 128.88(s), 137.62(s), 149.77(s), 163.88(s). MS 407 (M, 0.6), 195(100).

The enantiomer excess was 97% ee, as determined by HPLC using SUMICHIRAL OA-4500 (hexane/di chloroethane/ethanol: 60/30/10, 1=254:7.117 parts (S)-enantiomer, 8.247 parts (R)-enantiomer (principal component)).

As described in detail above, the present invention relates to a method for manufacturing an asymmetric fluorine-containing amine from a fluorine-containing carbonyl compound characterized in that a Schiff base obtained by the condensation of a fluorine-containing carbonyl compound and an asymmetric primary amine ((S)- or (R)-1-phenylethylamine) is treated with DBU or another appropriate organic base to perform an [1,3] proton shift reaction, and the resulting tautomeric imine is hydrolyzed to perform an asymmetric transamination reaction resembling an enzyme reaction. By utilizing an asymmetric transamination reaction resembling an enzyme reaction, the present invention makes it possible to readily synthesize an asymmetric fluorine-containing primary amine under moderate conditions and at a high yield (high asymmetric yield) by making use of a fluorine-containing carbonyl compound as a starting material. The resulting asymmetric fluorine-containing amine compound not only provides a useful substance displaying biological activity by itself but also lends itself to the use as a reagent for determining optical purity. It is also important as a synthesis intermediate of fine chemicals such as drugs, agricultural chemicals, and liquid crystals.

What is claimed is:

1. A method for preparing an asymmetric fluorine-containing amine compound from a fluorine-containing carbonyl compound, comprising contacting a Schiff base with an organic base, said Schiff base being a condensation product of a fluorine-containing carbonyl compound and an (S)- or (R)-1-phenylethylamine, followed by hydrolysis to result in an asymmetric transamination reaction thereby obtaining said asymmetric fluorine-containing compound.

2. The method according to claim 1, wherein said fluorine-containing carbonyl compound is of the formula

wherein $R_f$ is a $C_{1-16}$ linear or branched perfluoroalkyl group, and R is a $C_{1-16}$ linear or branched alkyl group or aralkyl group.

3. The method according to claim 1, wherein the Schiff base is (S)-N-(1-Phenyl-2,2,2-Trifluoroethylidene)-1-Phenylethylamine.

4. The method according to claim 1, wherein the Schiff base is (S)-N-(1,1,1-Trifluoro-3-Phenyl-Isopropylidene)-1-Phenylethylamine.

5. The method according to claim 1, wherein the Schiff base is (S)-N-(1,1,1-Trifluoroisopropylidene)-1-Phenylethylamine.

6. The method according to claim 1, wherein the Schiff base is (S)-N-(1,1,1-Trifluoroisobutylidene)-1-Phenylethylamine.

7. The method according to claim 1, wherein the Schiff base is (S)-N-(5,5,5,4,4,3,3-Heptafluoro-2-Pentylidene)-1-Phenylethylamine.

* * * * *

UNITED STATES PATENT AND TRADEMARK OFFICE
CERTIFICATE OF CORRECTION

PATENT NO. : 5,939,588
DATED : August 17, 1999
INVENTOR(S) : Vadim A. SOLOSHONOK, et al It is certified that error appears in the above-identified patent and that said Letters Patent is hereby corrected as shown below:

On the title page, item [73] should be:

-- [73] Assignee: Japan as represented by Director General of Agency of Industrial Science and Technology --

Signed and Sealed this

Twenty-third Day of May, 2000

Attest:

Q. TODD DICKINSON

*Attesting Officer*     *Director of Patents and Trademarks*